United States Patent [19]
Mager et al.

[11] Patent Number: 5,944,748
[45] Date of Patent: Aug. 31, 1999

[54] PHOTODYNAMIC THERAPY APPARATUS AND METHODS

[75] Inventors: David Mager, Leverett, Mass.; Harvey I. Pass, Novi, Mich.; Melvin Tecotzky, Mendham, N.J.

[73] Assignee: Light Medicine, Inc., Leverett, Mass.

[21] Appl. No.: 08/900,975

[22] Filed: Jul. 25, 1997

Related U.S. Application Data

[60] Provisional application No. 60/022,606, Jul. 25, 1996, provisional application No. 60/027,652, Oct. 4, 1996, provisional application No. 60/038,758, Feb. 21, 1997, and provisional application No. 60/038,756, Feb. 21, 1997.

[51] Int. Cl.[6] ................................................ A61B 17/36
[52] U.S. Cl. ................................. 607/88; 606/9; 606/11
[58] Field of Search ................................ 607/88, 90, 91, 607/92; 606/2, 10, 13, 15, 7

[56] References Cited

U.S. PATENT DOCUMENTS

| | | |
|---|---|---|
| 4,822,335 | 4/1989 | Kawai et al. . |
| 5,196,005 | 3/1993 | Doiron et al. . |
| 5,269,777 | 12/1993 | Doiron et al. . |
| 5,298,018 | 3/1994 | Narciso, Jr. . |
| 5,445,608 | 8/1995 | Chen et al. . |
| 5,474,528 | 12/1995 | Meserol . |
| 5,489,279 | 2/1996 | Meserol . |
| 5,505,726 | 4/1996 | Meserol . |
| 5,533,508 | 7/1996 | Doiron . |
| 5,567,687 | 10/1996 | Magda et al. . |
| 5,571,152 | 11/1996 | Chen et al. . |
| 5,572,996 | 11/1996 | Doiron et al. . |

FOREIGN PATENT DOCUMENTS

| | | |
|---|---|---|
| 3-261467 | 11/1991 | Japan . |
| WO 90/00914 | 2/1990 | WIPO . |
| WO 94/15666 | 7/1994 | WIPO . |

*Primary Examiner*—Linda C. M. Dvorak
*Assistant Examiner*—Roy Gibson
*Attorney, Agent, or Firm*—Lerner, David, Littenberg, Krumholz & Mentlik, LLP

[57] ABSTRACT

A device for applying light in photodynamic therapy is arranged to apply light in a pattern corresponding to the configuration of the lesion to be treated. The device may be customized in response to an image of the patient acquired before treatment. Alternatively, the device may include sensors for detecting a characteristic of tissue overlying each region of the device so that the device either emits light or does not emit light in each region depending upon the characteristics of the overlying tissue.

7 Claims, 3 Drawing Sheets

PHOTODYNAMIC THERAPY APPARATUS AND METHODS

CROSS REFERENCE TO RELATED APPLICATIONS

The present application claims benefit of U.S. Provisional Applications No. 60/022,606, filed Jul. 25, 1996, 60/027,652, filed Oct. 4, 1996; 60/038,758, filed Feb. 21, 1997; and 60/038,756, filed Feb. 21, 1997, the disclosures of which are hereby incorporated by reference herein.

FIELD OF THE INVENTION

The present invention relates to the field of photodynamic therapy.

BACKGROUND OF THE INVENTION

Photodynamic therapy involves the application of light to abnormal tissues (referred to herein as "lesions") in or on the body of a human or other mammalian subject to cause regression of the lesion. Ordinarily, a drug which increases the sensitivity of bodily tissues to light, referred to herein as a "photosensitizing agent" is administered before exposure of the tissues to light. When the light is applied to the tissues, chemical reactions which disrupt the normal function of the cells occur. This kills the tissues constituting the lesions. This process is applied, for example, in treatment of skin cancer and cancer of the internal organs. Preferred photosensitizing agents such as porphyrins tend to concentrate in cancerous tissues and increase the sensitivity of the cancerous lesion to light to a far greater degree than the increased sensitivity of the surrounding normal tissues. Thus, the cancerous lesion can be killed without destroying all of the surrounding normal tissues. The practice of photodynamic therapy is described, for example, in the article "Photodynamic Therapy in Oncology: Methods and Clinical Use", J. National Cancer Institute, Vol. 85, No. 6, pp. 443–456, March, 1993.

The treatment light used to perform photodynamic therapy commonly is administered through a hand-held device which is aimed by the physician during the treatment. For example, the light may be produced by a laser and guided through an optical fiber to a probe held by the physician. The physician can apply the light to the lesion by visually guiding the probe over the lesion. This approach works well for small, localized lesions. However, it necessarily depends upon the skill of the physician in observing the lesion and guiding the instrument. While some lesions are readily distinguishable from the surrounding tissue using ordinary visual observation, others are not. Also, where the lesions are widespread and located in an area with complex internal anatomy, it is difficult to direct the light onto all of the lesions. It is, therefore, likely that some lesions will remain untreated.

One approach which has been used to avoid these difficulties is simply to apply the treating light widely, on all of the tissues in the vicinity of the lesions. For example, as described in Tockner et al., Intrathoracic Photodynamic Therapy: A Canine Normal Tissue Tolerance Study and Early Clinical Experience, Lasers In Surgery and Medicine, 14:118–123 (1994) and in Pass et al., Use of Photodynamic Therapy for the Management of Pleural Malignancies, Seminars in Surgical Oncology 11:360–367 (1995), the treating light may be diffused throughout the surrounding tissues by filling an intrabody cavity with a light diffusing medium such as a liquid solution and directing the light into this diffusing medium. The light-directing instrument is also equipped with a diffusing optical system. This approach assures that the treating light will be delivered to all of the lesions. However, the treating light necessarily is also administered to surrounding normal tissues. Therefore, the dose of treating light which can be administered is limited to the dose which can be tolerated by the surrounding normal tissue.

Other proposals have been advanced for administering treating light in photodynamic therapy by means of light-emitting devices disposed within the body. Thus, Chen et al., U.S. Pat. No. 5,571,152 recites a "microminiature illuminator" with a light emitting diode and miniature microwave antennas. The microminiature illuminator assertedly can be injected into the interior of a tumor and can be actuated by RF power applied through the patient's tissues causing the LED to emit light within the tumor. Chen et al., U.S. Pat. No. 5,445,608, teaches other devices for PDT, including elongated probes with numerous LEDs thereon and a flat panel with multiple light emitting "vertical cavity surface-emitting lasers or," also referred to as "VCSELs" According to the '608 patent, multiplexing the VCSELs in time so that less than all sixteen are energized simultaneously minimizes the instantaneous current drawn by the devices. The devices have not been widely adopted in the art.

Other workers have sought to monitor the effectiveness of photodynamic therapy. Thus, Dorian, U.S. Pat. No. 5,533,508 and U.S. Pat. No. 5,572,996 disclose that tissues treated with photosensitizers will fluoresce when irradiated with the treatment light and that this fluorescence can be used as a measure of the efficacy of the treatment. Thus, when tissue treated with the sensitizer Photofrin-II is illuminated with treating light at 630 nm, the tissue will flouresce at about 690 nm and this fluorescence can be detected and used as a measure of the efficacy of the treatment.

Nonetheless, still further improvements in apparatus and methods for delivering photodynamic therapy would be desirable. It would be desirable to provide apparatus and methods which will concentrate the treating light on the lesion rather than on the surrounding normal tissues, without depending entirely on the skill and attention of the physician to accomplish this result.

SUMMARY OF THE INVENTION

The present invention addresses these needs. One aspect of the present invention provides methods of administering photodynamic therapy to a mammalian subject having a lesion in or on the body. The methods according to this aspect of the present invention include the step of positioning a light applying device capable of applying light throughout an application area over the lesion so that the application area of the device covers the lesion and also covers some normal tissue of the subject surrounding the lesion. According to this aspect of the invention, the device is actuated to apply treating light at a treatment wavelength selectively in regions of the application area aligned with the lesion and to not apply the light in regions of the application area which are aligned with normal tissue. The added specificity provided by this aspect of the invention facilitates use of photosensitizers which are not highly selective. Thus, relatively nonselective photosensitizers which have other desirable properties, such as high reactivity low toxicity, rapid clearing and reduced side effects can be employed.

The method according to this aspect of the invention may include the step of detecting the extent of the lesion using sensors disposed on the light emitting device itself and controlling actuation of the device during the actuation step responsive to this detected extent. The detecting step may include the step of detecting luminescence from tissues of the subject. Methods according to this aspect of the invention may include the step of administering a luminescent agent, such as a photosensitizing agent having an affinity for the lesion which is different from the affinity of the agent for normal tissue. Thus, the luminescent agent will provide a different degree of luminescence from the lesion than from the surrounding normal tissue. Where the luminescent agent is a photosensitizing agent, the luminescent agent preferably, has a greater affinity for the lesion than for normal tissues. The luminescence of the agent may be excited by applying light at an excitation agent different from the treatment wavelength, as by actuating a source of excitation wavelength light on the light applying device itself.

A further, related aspect of the invention provides light applying devices for use in photodynamic therapy. Devices according to this aspect of the invention include a support having a surface and means for emitting treating light at a therapeutic wavelength selectively from the surface so that the light is emitted only from selected regions of the surface. These devices further comprise means for detecting a characteristic of tissue of the subject overlying a plurality of locations on the surface of the support and providing signals representing the characteristic for the tissue overlying each such location. The characteristic is indicative of the presence or absence of a lesion overlying each such location. For example, the device may include means for detecting luminescence from the tissues overlying various locations on the surface. The device preferably includes means for actuating the light emitting means in response to the signals representing the characteristic of the tissue so that the emitting means emit the treatment light only at regions of the surface adjacent locations where the signals indicate presence of a lesion. For example, where the device include a plurality of electrically actuated light emitting elements such as light emitting diodes, the actuating means is arranged to supply power to only some of the diodes. The device may further include means for emitting excitation light at a wavelength different from the treatment light to provoke the luminescent response from the tissue. Alternatively, the characteristic sensed by the sensors may be a characteristic other than luminescence as, for example, temperature or radioactivity.

A method according to a further aspect of the present invention includes the steps of determining the configuration of the lesion to be treated as, for example, by conducting a CAT, MRI or other diagnostic scan which results in computer-intelligible data defining an image of the lesion and surrounding tissues, and then customizing a light applying device on the basis of the so-determined configuration. The customized device is especially adapted to apply light in a pattern of active areas corresponding to the configuration of the lesion. The customized device is applied to the subject so that the active areas of the device are aligned with the lesion. The device is then actuated to apply the treatment light only in the active areas. For example, where the configuration of the lesion includes areas of lesion interspersed with areas of normal tissue, the customizing step is performed so that the light applying device provides active areas interspersed with inactive areas. The customizing step may include the step of physically modifying the device, as by selectively applying a mask opaque to the treatment wavelength on areas of the light applying device corresponding to the inactive areas, or selectively removing such a material on areas corresponding to the active areas. Alternatively, the customization step can include the step of selectively removing parts of the light applying device so that the light applying device has a shape corresponding to the desired pattern of active areas, i. e., a pattern corresponding to the shape of the lesion. Where the light applying device includes an electroluminescent panel, portions of the panel may be removed. Thus, a device according to a related aspect of the present invention provides a support having a surface or surfaces with shape corresponding to the configuration of the lesion and means for providing treatment light at the treatment wavelength from this shaped surface.

Alternatively, the light applying device may have selectively actuable light emitting elements as discussed above. Such a device may be customized by applying control data to a programming element in the light applying device, so as to selectively enable and disable different ones of the light emitting elements.

Yet another aspect of the present invention provides a light applying device for use in applying photodynamic therapy to a mammalian subject including a support having a surface, means for emitting treatment light at a therapeutic wavelength from the surface and means for cooling the support. The support may have a cavity therein and the cooling means may include an at least partially solid fusible coolant disposed in the cavity, the coolant having a melting temperature less than about 50° C. and preferably between about 40 and about 50° C. Phase change of the coolant will maintain the device in the desired temperature even as substantial amounts of energy are applied through the device to apply the required dose of treating light. Alternatively or additionally, the support may include a coolant passage and the cooling means may include means for circulating a coolant into and out of the coolant passage. The device may include an elongated umbilical connector having proximal and distal ends and coolant passages in the umbilical connector connected to the coolant passages of the support. Where the light emitting means on the device are electrically actuated, the umbilical connector may include electrical conductors so that power and control signals can be supplied to the device along with the coolant.

The light emitting device may include various means for producing light, such as phosphorescent or luminescent materials or an array of light emitting diodes overlying the support. In a particularly arrangement for a diode-based device, the light emitting diodes are disposed substantially side by side so that the p-n junctions of the diodes extend substantially parallel to the surface. Preferably, these junctions overly at least fifty percent of the area of the surface. The device may further include conductors for conducting electrical power to the diodes and a biocompatible clear layer substantially transparent to the emitted treating light overlying the diodes. The conductors may include a first set of conductors disposed between the diodes and the support and a second set of conductors disposed between the diodes and the clear layer. The second set of conductors may be formed from a material such as indium tin oxide substantially transparent to the treating light whereas the support or the first conductors may be substantially reflective to the treating light. The diodes may be arranged in an array having rows and columns. The first set of conductors may extend along the rows, whereas the second set of conductors may extend along the columns, so that each diode is connected to one conductor of the first set and one conductor of the second set, allowing the diodes to be selectively addressed and illuminated.

These and other objects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 1:
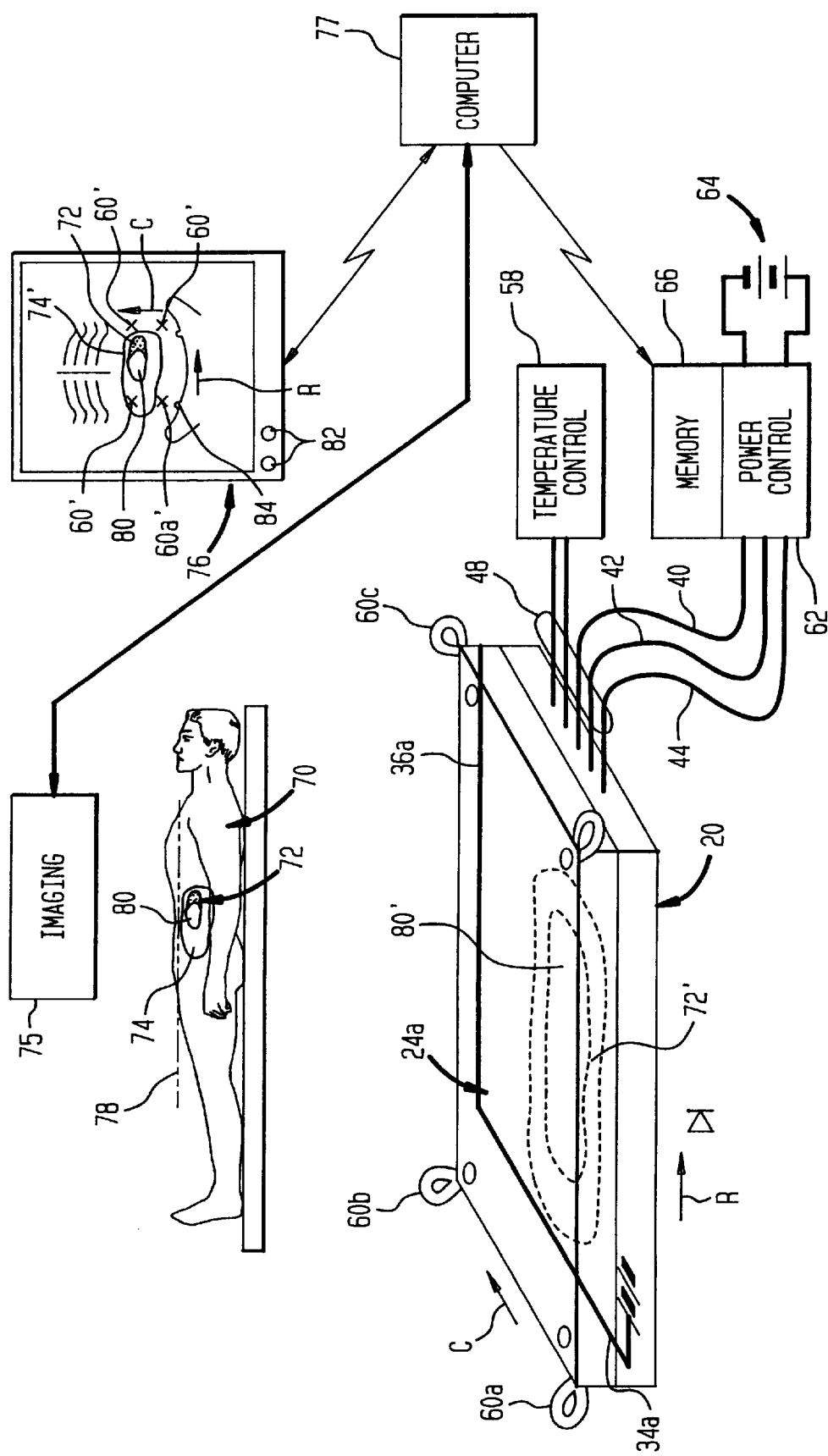
FIG. 1 is a diagrammatic view depicting elements of apparatus in accordance with one embodiment of the invention.

A device for administering photodynamic therapy in accordance with one embodiment of the invention includes a support 20 (FIGS. 1 and 2) which in this embodiment is a flat, paddlelike body. The support or body 20 has coolant passages 21 extending therein. Body 20 has a front surface 22 and a plurality of light emitting diodes or "LED's" 24 mounted on the front surface 22. Each diode 24 includes a p-type semiconductor layer 26 and an n-type semiconductor layer 28 overlying the p-type layer so that the p-n junction 30 defined by these adjoining layers extends generally parallel to the front surface 22 of support 20. Preferably, the p-n junctions of the diodes cooperatively cover at least a majority of the area of front surface 22 within the surface or region covered by the diodes. A clear dielectric layer 32 is disposed between the p-type layers 26 of the diodes and support 20. The clear dielectric layer has a reflective, metallized coating on its surface facing away from diodes 24 and towards support 20. A transparent filler material such as a clear epoxy 27 is disposed in the spaces between individual diodes 24.

Figure 2:
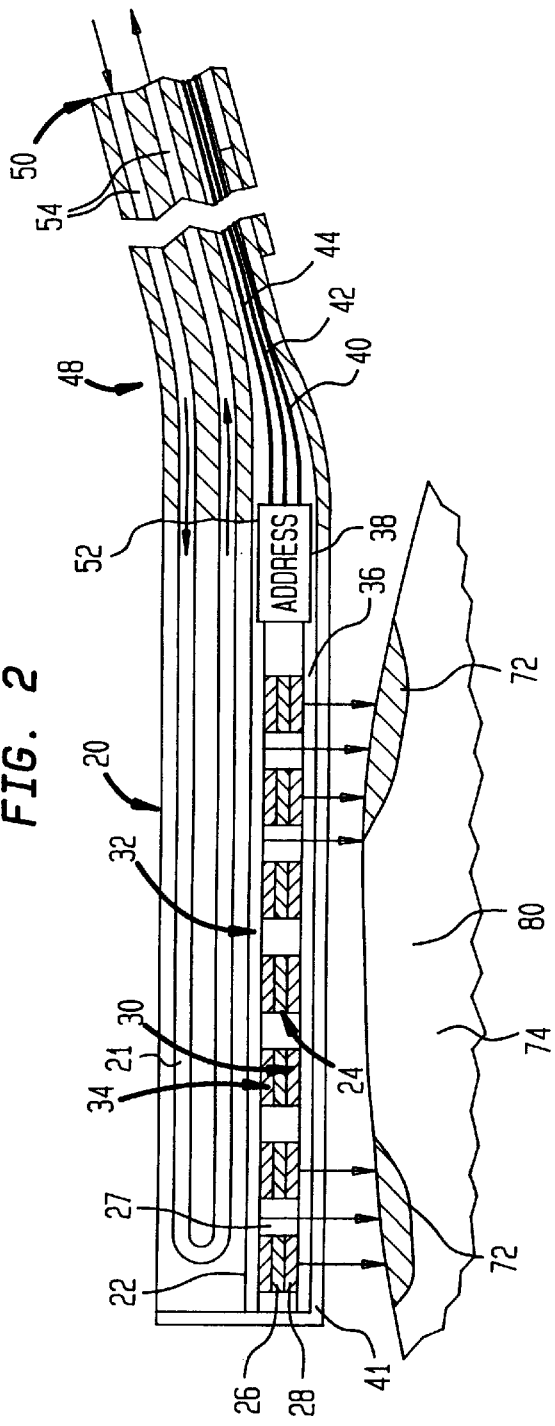
FIG. 2 is a diagrammatic sectional view depicting part of the apparatus of FIG. 1 during one stage of a treatment method, the device being inverted relative to the position depicted in FIG. 1.

The sizes of the diodes and of their individual layers are greatly exaggerated in FIG. 2 for clarity of illustration. In actual practice, numerous diodes are provided. For example, a device about 7.5×12.5 cm may include about 1000 or more diodes. The diodes are arranged in rows and columns orthogonal to the rows. A plurality of column conductors 34 provided. The column conductors extend in a column direction perpendicular to the plane of the drawing in FIG. 2. A few of the column conductors are shown schematically in FIG. 1. Column conductors 34 are composed of a material such as aluminum or another metal which is electrically conductive and which reflects light at the wavelengths to be produced by the diodes. The column conductors 34 are disposed between the p-type layers 26 of the individual diodes 24 and the dielectric layer 32 so that each diode 24 overlies and is electrically connected to one column conductor 34.

The device further includes a plurality of row conductors 36 overlying the surfaces of diodes 24 remote from dielectric layer 32 and support 20, only one such row conductor being visible in FIG. 2. The n-type layer 28 of each diode 24 is in contact with one row conductor 36. Row conductors 36 are composed of a material which is electrically conductive but which is substantially transparent or translucent to the light which will be emitted by the LEDs. For example, with infrared-emitting LEDs, row conductors 36 may be formed from thin strips of indium tin oxide ("ITO"). A few of the row conductors 36 are depicted schematically in FIG. 1. Thus, each diode can be individually addressed by one row conductor and one column conductor. For example, a particular diode 24a at the intersection of row conductor 36a and column conductor 34a (FIG. 1) can be illuminated by applying an electrical potential between these two conductors. Row conductors 34 and column conductors 36 are connected to an addressing chip 38. Addressing chip 38 is arranged to connect power input conductors 40 and 42 (FIG. 2) to individual row and column conductors as specified by information supplied on a data conductor 44. Addressing chip 38 may be of the type similarly used for actuating two dimensional LED arrays for computer display purposes. Although data line 44 is shown as a single conductor, it should be appreciated that the data line may include plural conductors as required in a serial or parallel data communications bus.

A clear, biocompatible coating or top layer 41 overlies the front or top surfaces of diodes 24 remote from the support 20 and also overlies the clear filler material 27. Thus, light emitted by any individual diode can propagate through the top surface of the diode and through the overlying row conductor 36 and the top layer. Some of the light may propagate towards the rear or bottom surface of the diode and will be reflected by the underlying column conductor 34. Still other light may exit from the sides of the diode, at the edge of the P-N junction or this light will be reflected by the coating on dielectric layer 32 through the clear filler material 27. Thus, substantially all of the light emitted by each diode will pass out through the top or front of the device in the vicinity of the emitting diode. Layer 41 desirably includes a diffuser, such as small particles of $Al_2O_3$ dispersed in the layer or a rough surface so as to distribute the light from each LED over a small region surrounding that LED and thereby assure even illumination in the area between adjacent LED's.

Support 20 is physically connected to a distal end 52 of a flexible, elongated umbilical connector 48 having a proximal end 50 remote from the support. Connector 48 may be in the form of a multi-lumen tube having a pair of coolant passages 54 extending between its proximal and distal ends, the coolant passages 54 being in communication with the coolant passages 21 of support 20. The electrical power conductors 40 and 42 and data conductor 44 associated with the LEDs and address chip 38 also extend through a bore in umbilical connector 48 to the proximal end 50 of the umbilical connector.

The coolant passages 54 of the umbilical connector are connected to a temperature control device 58 incorporating conventional pumps (not shown) for circulating a coolant such as water through the cooling passages of the umbilical and hence through the cooling passages of the support. Temperature control device 58 is also provided with a refrigeration unit or with a source of pre-chilled coolant and with appropriate, conventional thermostatic controls for maintaining the circulating coolant at a preselected temperature. The temperature control device 58 may also be provided with electrical resistance or other forms of heaters, also controlled thermostatically, for preheating the coolant and hence preheating support 20 to an elevated temperature as described below. Other, simpler forms of temperature control simply route coolant from a source through the cooling passages of the device to waste.

Support 20 has a plurality of suturing rings 60 mounted at predetermined locations around the periphery of the support. Suturing rings 60 are disposed in predetermined spatial relationship to the array of diodes 24.

The electrical conductors extending through umbilical connector 48, including the power conductors 42 and 40 and data line 44 are connected to a power controller 62. Controller 62 includes a power supply 64 connected to the power conductors 42 and 40, and also includes a memory 66. Power control 62 is arranged to read designations of LEDs to be illuminated from memory 66 and to send appropriate signals through data line 44 to actuate the address chip 38 and cause illumination of the particular LEDs specified by the data.

In a method according to one embodiment of the invention, a mammalian subject such as a human medical patient 70 having a tumor or other lesion 72 on an internal organ 74 is imaged prior to treatment by a conventional medical imaging apparatus such as magnetic resonance imaging, X-ray, CAT, PET, radioisotope imaging or other conventional medical imaging modality. The lesion may be partially removed or "debulked" surgically in the normal fashion before administration of photodynamic therapy. The debulking procedure may be performed before or after the imaging step. The imaging device is arranged to produce a computerized map of the body representing one or more physical characteristics such as x-ray density, T-1 or T-2 weighted proton density, radioactivity or the like. A planar representation of the computerized image data representing the structures of the patient's body lying on a hypothetical cutting plane 78 is depicted on a conventional display apparatus 76. The imaging device 75 is arranged to store and manipulate the images through a conventional imaging control computer 77. Computerized imaging devices of various types are well-known. Where the imaging device collects a three-dimensional set of data representing volume elements or "voxels" distributed throughout a three-dimensional region of the patient's body, the imaged plane may be selected arbitrarily by the user. In other imaging modalities such as X-ray, the image plane is determined by the mechanical structure of the apparatus and the placement of the patient relative to the apparatus.

In the particular patient depicted, lesion 72 covers a region of an internal organ 74, but does not cover the entirety of that region. Thus, seen in the particular imaging plane, lesion 72 has a hole 80 in its center. The tissue in hole 80 is normal, healthy tissue. The display device incorporates computer input controls 82 linked to computer 77. The computer and imaging device are arranged to display a representation of support 20, in this case a representation of four discrete points 60' corresponding to the suturing hole 60 at the corners of the support. Any other form of visual representation can also be used. By manipulating the computer input controls 82, the operator can move the representation of the support within the displayed image and can change the orientation of the support in the image as desired. The operator uses these controls to align the representation of the support with the depiction of the lesion 72 in the displayed image. Once the representation of the support has been aligned with the depiction of the lesion, the computer has data defining the desired location of the support in the frame of reference of the computer image, including data correlating directions in the frame of reference of the support, such as the row and column directions R and C with the directions in the frame of reference of the image. The computer also has data defining the locations covered by the lesion 72 in the frame of reference in image. The computer thus can calculate the locations occupied by the lesion in the frame of reference of the support, i.e., in the row and column directions on support 20, assuming that the support is placed in the location depicted on the image. Thus, the computer can calculate the distances in row and column directions R and C from the starting point, assumed to be suture loop 60a, to the locations of particular voxels occupied by the lesion. Those locations in dimensions R and C correspond to the spots on the surface of the support which will be aligned with the tissue constituting the lesion when the support is positioned within the patient's body at the position depicted in the image. The locations in the row and column dimension R and C in turn correspond to identities of individual diodes which should be illuminated to illuminate only the tissue constituting the lesion. Computer 77 stores this data and transmits it to the memory 66 of the power control computer associated with the illuminating device. This effectively sets the device to provide illumination in a customized pattern corresponding to illumination of diodes in a pattern 72' having the same shape and size as the lesion. For example, the pattern of illuminated diodes 72' has a hole 80' corresponding to the hole 80 in the lesion itself.

The computer display also shows the location of the support relative to other organs and landmarks within the body. For example, by observing the display, the physician can note the desired location of suturing loop 60a relative to a prominent bony structure 84 in the body of the patient. Similarly, the surgeon can note the locations of the other suturing loops in the image relative to other prominent surgical landmarks. The suturing loops thus act as fiducial markers on the device, so that the device can be positioned in a precise location. Any other feature or mark on the device which is disposed in a fixed location relative to the LED's can be used in a similar manner.

In the next stage of the process, a conventional photosensitizer is administered to the subject. Support 20 is placed within the body of the patient at a location found as discussed above. Thus, each of the suturing loops is placed at the appropriate location relative to the surgical landmarks noted in the image. Umbilical connector 48 extends into the patient's body. The proximal end of the umbilical connector remains outside of the body and hence remains available for connection to temperature control unit 58 and electrical control unit 62. Once the support has been aligned in position with the patient's body, the control unit is actuated to illuminate the diodes in the appropriate pattern. Notably, only those diodes in the region 72' corresponding to the lesion itself are illuminated. Other diodes, such as those in the region 80' aligned with the hole 80 are not illuminated. This assures that light from the diodes is applied on the regions constituting the lesions and that very little or no light is applied to the surrounding normal tissue. The light emitting diode which are energized, i.e., those in regions 72' corresponding to the configuration of the lesion, emit light at a wavelength which is absorbed by the photosensitizer. Where the photosensitizer is a conventional photosensitizer such as a porphyrin or porphyrin derivative, the LED's typically are arranged to emit light at about 610–650 nm, most typically at about 630 nm. Such light tends to penetrate through tissues to a greater depth than light at other wavelengths and is also strongly absorbed by the conventional photosensitizers. For use with conventional photosensitizers, the LED's may be formed from doped aluminum indium gallium phosphide (ALINGAP) to provide peak emission at about 630 nm. A conventional aluminum gallium arsinide (ALGAS) LEDs having a peak emission at about 645 nm may also be employed.

A device, about 7.5 by about 13 cm with only 1,000 LED's may draw on the order of 60 watts of electrical power when all of the LEDs are illuminated simultaneously, so as to provide about 1 watts total light output and provide about 25 joules/cm² in about 40 minutes. If only some of the LEDs are illuminated, the amount of electrical power dissipated is reduced proportionately. Nonetheless, the device will produce substantial amounts of heat. Preferred devices include more LED's per unit area and generate even more heat. Heating is commonly considered beneficial in photodynamic therapy because hypothermia tends to accentuate the effects of photodyamic therapy. However, the temperature of the device cannot be allowed to rise to levels which will damage the surrounding, normal tissue. The cooling provided by temperature control unit 58 and the coolant circulated through the coolant passages is adjusted to keep the temperature of the device at the desired level, typically about 40° C. Where the temperature control incorporates heating, the circulating fluid or coolant can be preheated so as to bring the device to an elevated temperature before the device is placed into the body, or after placement in the body but before administration of the light. Thus, the light may be provided in conjunction with hypothermia from the beginning of the light-administering step. As the process proceeds and as heat is evolved by the illuminated LEDs, the temperature control unit can cool the fluid to maintain the device at a substantial stable temperature throughout the process.

Because the device concentrates the applied light on the diseased tissue, it minimizes damage to the surrounding normal tissue. Further, because the photodynamic therapy is administered at many locations simultaneously, the process can be completed rapidly.

Figure 3:
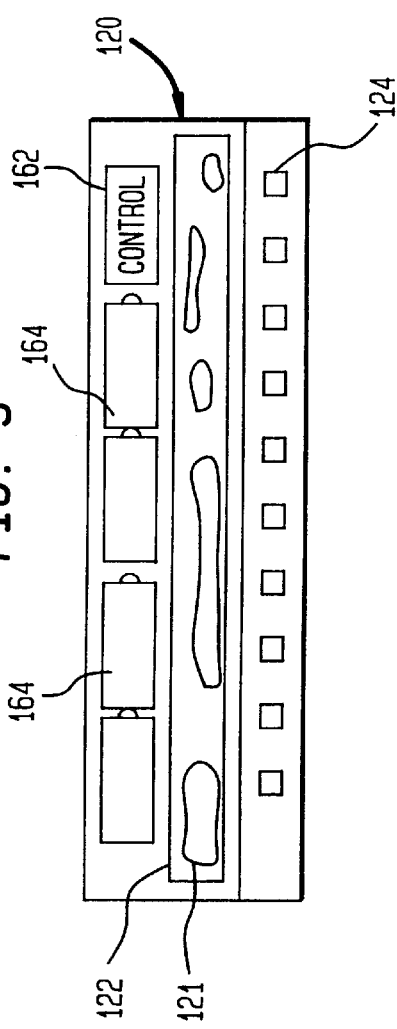
FIG. 3 is a diagrammatic sectional view depicting apparatus in accordance with a further embodiment of the invention.

Apparatus in accordance with another embodiment of the invention is schematically depicted in FIG. 3. This apparatus is similar to the apparatus in FIGS. 1 and 2, except that the apparatus is powered by internal storage batteries 164 and the control unit 162 is also mounted within the support. Batteries 164 may be nickel cadmium, nickel hydride lithium, or other relatively high-energy density primary (nonrechargeable) or secondary (rechargeable) cells. For an LED device which is adapted to deliver about 35 joules/cm² of surface area, a nickel cadmium battery about 1 cm (0.4 inches) thick would provide sufficient energy. For example, in a 7.5 by 13 cm (3 inch by 5 inch) device, approximately 40 watt hours of electrical energy would be required in a nickel cadmium battery, approximately 7.5 by 13 cm and approximately about 4 cm thick would provide this energy. Internal control unit 162 is provided with the appropriate data specifying the placement of the LEDs to be illuminated by a temporary computer link, which is disconnected before the device is placed within the body of the subject.

The device illustrated in FIG. 3 also has a fusible material 121 disposed in a chamber 122 within the support 120. The fusible material has a liquidus temperature at or about the upper limit of the temperature to be maintained by the device during use. In use, as the LEDs generate heat, the fusible material melts. The heat generated by the LEDs is absorbed in the heat fusion of the fusible material. Therefore, the temperature of the device remains substantially stable during operation. Suitable fusible materials having melting points in the vicinity of 40° C. include the following:

Organic compounds:
Acetic acid, 2-nitrophenyl ester
Acetic acid, bromodifluoro—F2BrCCO2H
Acetophenone α-bromo-3 chloro-—C8H6BrClO
Benzaldehyde, 2-hydroxy-4-methoxy—C8H8O
Benzene, 1-amino-4-dimethylamino—C8H12N2
Benzene, 1(bromomethyl)-3,5-dimethyl—C9H11Br
Benzene, 4-chloro, 1,2 dinitro—C6H3ClN2O4
Benzene,1,3,diiodo—C6H4I2
Benzoic acid, 3-chloro, nitrile—C7H4ClN
Butane, 1,2,3,4 tetrabromo—BrCH2CHBrCHBrCH2Br
Inorganic Compounds
Ammonium iron sulfate—NH4Fe(SO4)2.6H2O
Ammonium propionate—NH4C3H5O2
Beryllium stearate—Be(C18H35O2)2
Borotungstic acid—H6BW12O40.30H2O
Calcium bromide, hexahydrate—CaBr2.6H2O
(non-inclusive listing)
Mixtures of metals
K (30%) Na (70%)
Na (50%) Hg (50%)

Numerous other fusible materials can be used. Ordinary ice can be employed.

Figure 4:
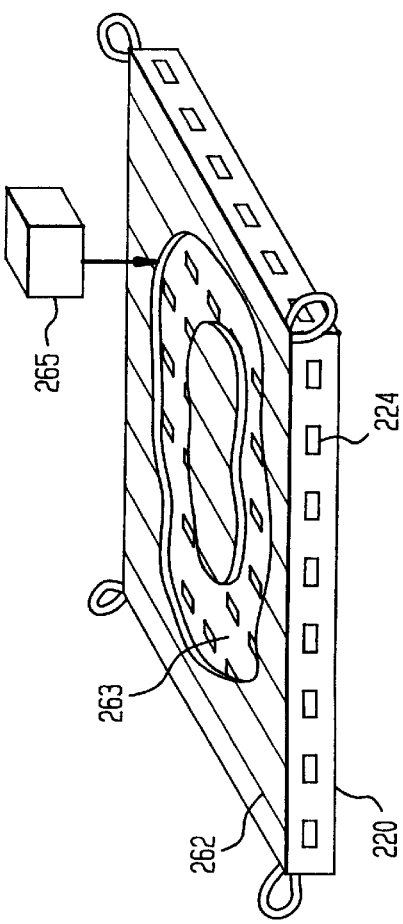

A device according to a further embodiment of the invention, depicted in FIG. 4, includes an array of light emitting diodes 224 covering a front surface of a support 220 as discussed above. The electrical components of the apparatus (not shown) are arranged to eliminate all of the diodes nonselectively, either simultaneously or in a sequential pattern. The device further includes a layer of an opaque masking material 262 overlying the array of light emitting diodes. Masking material 262 is patterned in a pattern corresponding to a negative image of the lesion. Thus, the opaque material layer has openings 263 in the areas where emission of treating light is desired. In other areas of the surface, the treating light is blocked by the masking material and is not emitted. Thus, the device is adapted to emit the treating light in a configuration corresponding to the configuration of the lesion to be treated.

In a method according to a further embodiment of the invention, a device as depicted in FIG. 4 is prepared based upon computerized image data. Thus, in the manner discussed above with reference to FIGS. 1 and 2, a computerized image of the patient is acquired and the computer system generates a map of locations on the surface of support 220 where emission is desired and where emission is not desired. A computer actuated manufacturing process such as an ink jet printer 265 applies the opaque masking material selectively on the locations where emission is not desired. Alternatively, the computer actuated process may include development of a photoresist in patternwise fashion or operation of a laser or computer controlled machine tool to remove the opaque masking material in regions where application of the treatment light is desired.

Figure 5:
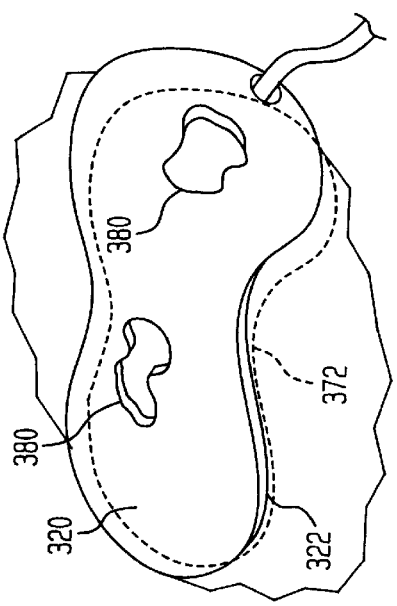
FIGS. 4 and 5 are diagrammatic perspective views depicting apparatus in accordance with still further embodiments of the invention.

The device depicted in FIG. 5 includes a flexible support 320 with a continuous light emitting layer or layer structure 322 disposed on its active surface. The continuous light emitting layer may include an organic or inorganic electroluminescent panel. Alternatively or additionally, the continuous light emitting layer may include a layer of a phosphor or other luminescent material such as a phosphor responsive to β radiation or a chemiluminescent phosphor to emit the treating light at the desired wavelength. UV-energized phosphors having long decay times may also be used. In this case, the device preferably is removed from the subject and charged by exposure to UV light. It will continue to emit the treating light after such exposure. Some of the phosphors which can be used are set forth in Table 1, below.

TABLE I

PHOSPHORS

| Chemical formulae | Manufacturer | Wavelength (nm) | Bandwidth at 50% (nm) | Conversion Efficiency | Excitation | Decay (sec) | Density (g/cc) |
|---|---|---|---|---|---|---|---|
| Y2O3:Gd | | 312 | 5 | | electrons, Xrays | | |
| LaOBr:Gd3 | | 320 | 5 | | | | |
| YTaO4 | Sterling | 330 | 100 | | Xray | | 7.57 |
| BaFCl:Eu (1%) | | 390, 750 | 50 | 13% | electrons, Xrays | | 4.56 |
| YTaO4:Nb (2%) | Sterling | 410 | 100 | | Xray | | |
| ZnS:Ag (P-7 Blue, P-22 Blue) | | 420 | 60 | 21% | Electrons | | |
| CaWO4 | | 430 | broad | 3–5% | Xray | | 6.12 |
| CaAl2O4:Eu | Nemoto | 440 | 50 | | UV-light | 28000 | |
| Sr5Cl(PO4)3:Eu | Sylvania 247 | 447 | 32 | | UV | 4.00E−07 | 4.2 |
| BaMg2Al16O27:Eu | Sylvania 2461 | 450 | 49 | | UV | 5.00E−07 | 3.7 |
| CaSrS:Bi | Nemoto | 454 | | | UV-light | 28,000 | |
| Sr2P2O7:Sn | Sylvania 243 | 460 | 105 | | UV | 6.70E−06 | 3.5 |
| MgWO4 | Sylvania 2301 | 473 | 60 | | UV | 4.60E−05 | 6.8 |
| BaAl2O4:Eu, Nd | Nemoto | 490 | 80 | | UV | 28,800 | |
| BaAl2O4:Eu, Sm | Nemoto | 500 | 75 | | UV | 28,800 | |
| Sr0.5Ca0.5Al2O4:Eu, Dy | Nemoto | 500 | 80 | | UV | 28,800 | |
| Y2O2S:Pr+3 | | 512 | | 11% | Electrons, Xrays | | |
| Gd2O2S:Pr | USRO | 515 | 20 | 9–11% | Xray, electrons | | |
| SrAl2O4:Eu Luminova Yellow-Green | United Mineral | 520 | 75 | | UV-light | 120000 | 3.65 |
| Zn2SiO4:Mn, As | USRO | 520 | 40 | 9% | Electrons | 0.139 | |
| ZnS:Cu | Hanovia, USR Optnix | 530 | | 23% | UV, Light | 28800 | |
| ZnSCdS:Cu, Al | P-22 Green | 540 | 75 | | Electrons | | |
| Gd2O2S:Tb+3 (1%) | Sylvania | 545 | 2 | 16% | Xray, electrons | | 7.34 |
| La2O2S:Tb+3 (Prr) | | 545 | 1 | 13% | Xary, electrons | | |
| InBO3:Tb | | 545 | | 8% | Electrons | | |
| LaOCl:Tb | | 545 | | 10% | Electrons | | |
| Y3Al6Ol2:Tb | | 545 | | 8% | Electrons | | |
| Y3(Al,Ga)5O12:Tb | | 545 | | 9% | Electrons | | |
| Y2SiO3:Tb | | 545 | | 9% | Electrons | | |
| ZnSCdS:Cu | P-14 Orange | 570 | 100 | | | | |
| Y2O3:Eu+3 | Sylvania 23442 | 611 | 0.6 | 7–8% | UV, Xray, electrons | 1.10E−03 | 5 |
| CaSiO3:Pb:Mn | Sylvania 290 | 615 | 86 | | UV | 3.20E−02 | 3 |
| YVO4:Etu+3 | | 618 | | 7% | Electrons | | |
| YVO4:[V]:Eu | Sylvania 2391 | 619 | 0.6 | | UV, electrons | 6.20E−04 | 4.3 |
| Gd2O2S:Eu | Sylvania, USRO | 625 | 20 | 9–10% | electrons, Xrays | | |
| Y2O2S:Eu+3 (<6%) | USR P-22 RE 555 | 625 | 3 | 9–10% | UV, Xray, electrons | | |
| Y2O2S;Eu+3 (P Red) | Sylvania 1152 | 625 | 3 | 9–10% | UV, Electrons, Xrays | | 4.9 |
| (Sr,Mg)3(PO4)2:Sn | Sylvania 282, 283 | 626 | 138 | | UV | 1.90E−05 | 3.8 |
| Zn(PO4):Mn | Sylvania 141 | 639 | 90 | 8% | Electrons | | |
| Zn3(PO4)2:Mn | Sylvania 141 | 639 | 90 | 8% | Electrons | medium | |

TABLE I-continued

PHOSPHORS

| Chemical formulae | Manufacturer | Wave-length (nm) | Bandwidth at 50% (nm) | Conversion Efficiency | Excitation | Decay (sec) | Density (g/cc) |
|---|---|---|---|---|---|---|---|
| $Mg_4(F)(Ge,SN)O_6:Mn$ | Sylvania 2364 | 658 | 16 | | UV | 3.50E-03 | 3.9 |
| $Mg_4(F)GeO_6:Mn$ | Sylvania 236, | 658 | 14 | | UV | 2.30E-03 | 3.8 |
| $Li_2Al_2O_4:Fe$ | Syvlania 232 | 743 | 83 | | UV | 1.40E-02 | 2.5 |
| $YVO_4:Nd$ | Sylvania 2373 | 880 | | | electrons | | |
| $CaWO_4[W]$ Pb | Sylvania 2402, 2412 | 433, 446 | 114 | 5% | UV, Xray | 1.20E-05 | 6.4 |
| $LaOBr:Tm+3$ (2%) | GE | 470, 370, 300 | 5 | 11% | Xray | | 6.1 |
| $LaOBr:TB+3$ | GE | 540, 440, 420, 380 | 5 | 14% | Xray | | |
| $Y_2O_2S:Tb+3$ | USRO | 545, 420+ | 2 | 18% | | | |
| $CaSrS:Bi$ | | Blue | | | UV, light | 600+ | |
| $HfGeO_4:Ti$ | | Blue | broad | | Xray | | 8.5 |
| $HfO_2:Ti,Ln,M$ | Kodak | Blue | broad | | Xray | | 10.1 |
| $Li_2HfO_3:Zr,SN,Ti,Ln$ | Kodak | Blue | | | Xray | | 6.6 |
| $ZnS:Ag$ (<0.5%) | USR 2205 | Blue | | | UV | | 4.1 |
| $Li_3TaO_4:Nb$ | | Blue | | | Xray | | |
| $LuTaO_4:Nb$ | | Blue | | | Xray | | |
| $Mg_4Ta_2O_9:Nv$ | Kodak | Blue/UV | Broad | | | | 6.2 |
| $(ZnCd)S:Ag$ (Green) | | Green | | 20% | Electrons | | |
| $ZnS:Cu$ (<0.5%) | USR 2210 | Green | | | UV | | 4.1 |
| $ZnS:Cu$ (<0.5%) | USR 2330 | Green | | | UV, Light | 28800 | 4.1 |
| $CaS:Bi$ | | violet-blue | | | UV, light | 600+ | |
| $ZnS:Ag$ (<0.5%) | USR 2200 | White | | 21% | UV, Electrons | | 4.1 |
| $ZnS:Cu; ZnS;Mn:Cu$ | Sylvania 70, 830 | White | | | EL | | 4.1 |
| $ZnS:Cu,Mn$ | USR 1481-95 | Yellow | | | UV | | |
| $ZnS:Mn$ (<0.5%) | USR 3336 | Yellow Orange | | | UV | | 4.1 |
| $ZnCdS:Cu$ | | Yellow or Orange | | | UV, ligh | 600+ | |
| $CaO:Mn$ | | | | 5% | | | |
| $CaS:Ce+3$ | | | | 22% | | | |
| $CaSiO_3:Pb:Mn$ | | | | | | | |
| $ZnO:Zn$ | | | | 7% | | | |

Radioactive materials which can be utilized to power an electron-activated phosphor include those listed in Table II below:

TABLE II

| ISOTOPE | ATOMIC WEIGHT | HALF LIFE (days) | MAX DECAY ENERGY (Mev) | β POWER |
|---|---|---|---|---|
| H3 | 3 | 4,475 | 0.01861 | 0.328 w/gm |
| P32 | 32 | 14 | 1.71 | 1,667.0 w/gm |
| Ru106 | 106 | 367 | 0.0394 | |
| Sn123 | 124 | 125 | 1.42 | |
| W185 | 185 | 77 | 0.432 | |
| T1204 | 204 | 1,380 | 0.763 | |
| Sr90 | 90 | 10,257 | 0.546 | |
| P33 | 33 | 25 | 0.248 | 70 w/gm |
| Bi210 | 210 | 5 | 1.16 | |
| Sulfur 35 | 35 | 87 | 0.164 | 12.4 w/gm |
| Sr89 | 89 | 50 | | |

The more preferred radioactive materials are those which emit electrons at less than about 35 keV, and preferably at about 30 keV or less, and which have decay energies less than these values. For this purpose, tritium ($^3H$) is the most preferred isotope. Tritium desirably is present as a chemically stable tritium based compound which has a high density of tritium per unit volume, such as tritium-substituted water (tritium density of 0.27 gram/cm$^3$), lithium hydride (0.246), Decaborane—(0.2632), ammonium bromide—(0.275), and titanium hydride (0.43). If isotopes having greater decay energies are employed, the resulting particles will emit X-rays along with light. Such X-rays can be utilized as part of the treatment regime. The most preferred high-energy β isotope is $^{35}$S.

In a method according to a further aspect of the invention, support 320 and the continuous light emitting layer or layer structure are trimmed to a shape corresponding to the configuration of the lesion to be treated. Thus, as depicted in FIG. 5, the borders of the support 320 and active light emitting layer 322 have been trimmed to a shape corresponding to the shape of lesion 372. Holes 380 have been formed in areas corresponding to regions of normal tissue disposed within the lesion. Here again, the light emitted by the device is concentrated on the lesion and the normal tissue is substantially unaffected. Luminescent materials as discussed above with reference to FIG. 5 may also be used in the methods and apparatus using selective masking as discussed with reference to FIG. 4.

Figure 6:
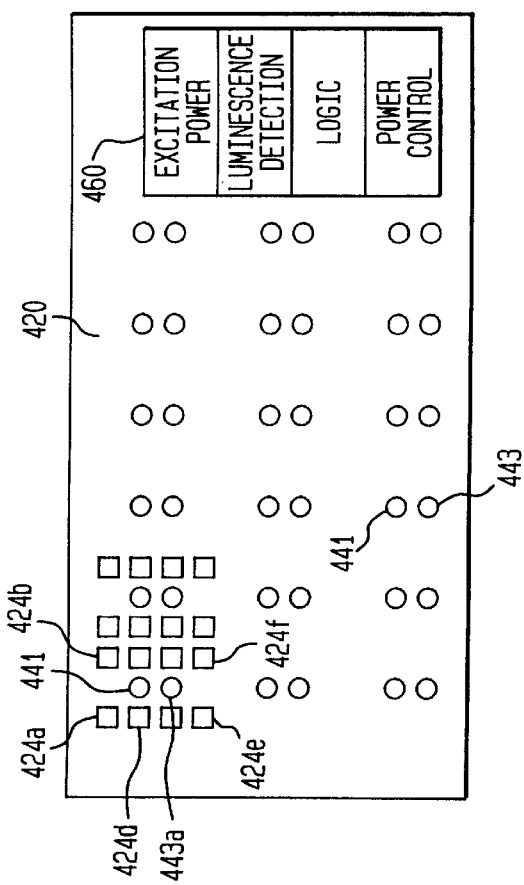
FIG. 6 is a diagrammatic view depicting apparatus in accordance with yet another embodiment of the invention.

A device according to a further embodiment of the invention is depicted in FIG. 6. This device includes an array of treating LEDs 424 disposed on the active surface of a support 420 in a manner similar to that discussed above with reference to FIG. 1. Only a few of the LEDs 424 are depicted in FIG. 6. In actual practice, numerous LEDs are provided substantially covering the active surface. The device of FIG. 6 further includes excitation LEDs 441 and sensors 443 mounted on the active surface and interspersed with treating LEDS 424. Each excitation LED 441 is disposed adjacent to one photocell 443. Each photocell 443 is adjacent to a particular group of photocells 424. For example, photocell 443a is surrounded by a set of treating LEDs including LED 424a, 424b, 424d, 424e and 424f. Excitation LEDs 441 are adapted to emit excitation light at an excitation wavelength different than the treating wavelength and, preferably, substantially shorter than the treating wavelength. The excitation wavelength is selected so that it will be absorbed by photosensitizer-laden tissue and so that the photosensitizer-laden tissue will fluoresce under the influence of the excitation light. For example, where porphyrin-based photosensitizers are employed, the excitation light may be applied at about 410 nm wavelength. Photocells 443 are adapted to receive light at the wavelength emitted by the photosensitizer-laden tissue during such fluorescence. Again, where conventional porpherin-based photosensitizers are employed, photocells 443 may be adapted to receive light at about 630 nm wavelength. Preferably, photocells 443 are provided with selective optical filters which block other wavelengths.

The device further includes electrical power and control unit 460. The power and control unit is linked to the individual excitation LEDs 441 and photocells 443. The power unit is adapted to actuate the excitation LEDs and detect the resulting luminescence or fluorescence of the tissues at each photocell 443. The logic unit associated with controller 460 determines whether the luminescence observed by each photocell is above or below a preselected threshold. If the luminescence observed by a particular photocell 443 is above the threshold, the logic unit instructs the power control unit to illuminate the treating LEDs 424 in the group surrounding that particular photocell. Otherwise, the logic and power control units prevent illumination of that particular group of photocells. As mentioned above, typical photosensitizers tend to concentrate in malignant tumors. Therefore, the tumor will fluoresce to a substantially greater degree than the surrounding normal tissue. Thus, by applying the excitation light and detecting the resulting fluorescence, the device measures a characteristic of the tissue overlying the location of each photocell 443 and provides signals indicating the presence or absence of the malignant lesion overlying each such location. A signal indicating a relatively high degree of luminescence indicates the presence of a lesion whereas a signal indicating a relatively low degree of luminescence indicates the absence of the lesion. The device controls the treating LEDs 424 to apply treating light only at those regions of the surface adjacent to those locations where the photocell signals indicate the presence of the lesion.

In methods employing devices according to this embodiment of the invention, there is no need for a preliminary mapping or imaging step. Instead, the physician simply applies the device on the subject in the general vicinity of the lesion, so that the active surface of the device overlies the lesion. The device automatically selects particular regions of its surface which are aligned with the lesion and emits the treating light at those regions. Those regions of the device surface which are aligned with normal tissue do not emit the treating light.

To increase the sensitivity of the photocells, the excitation light from excitation LEDs 441 may be modulated with a predetermined modulation frequency and the luminescence detection circuits which receive the signals from photocells 443 may include frequency selective filters. This greatly enhances the ability of the device to reject unwanted signals due to stray light. The steps of applying the excitation light and detecting the resulting fluorescence or condition-sensitive signals may be repeated during the treatment process. Thus, if the device moves during the treatment process relative to the patient, the pattern of illumination on the surface of the device will change so that at each moment only those regions of the device surface aligned with the lesion are illuminated, whereas those regions aligned with normal tissues are not illuminated.

The excitation light may be provided by devices other than LEDs as, for example, by fiber optic transmission from outside of the body from phosphors or chemoluminescent reactions. In a variant of this approach, the treating LED's 424 can be used to apply the excitation light. Thus, a brief dose of treating light can be applied as the excitation light, nonselectively over the entire surface of the support. Luminescence provoked by the treatment light may be detected to provide the condition sensing signals. The treating LED's can also be used as the detectors for sensing the flouresecence of the tissues. Also, condition-sensing devices other than luminescence detecting devices may be employed. For example, if the lesion to be treated has a higher or lower temperature than the surrounding normal tissue, temperature sensing devices such as thermistors or thermocouples may be provided on the surface of support 420 and the logic unit may be arranged to treat signals indicating a particular range of temperature as indicating the presence of the lesion. Alternatively, a radioactive tracer which is absorbed by the lesion to a greater degree than by normal tissue can be administered to the patient. The device may include a plurality of radiation-response detectors such as scintillation detectors, and may treat signals indicating a relatively high degree of radioactivity indicating a presence of the lesion in a particular lesion.

Although the logic unit is depicted in FIG. 6 as integrated into the support, the logic unit used in association with the excitation and sensing devices may be physically mounted outside of the body and may be connected to the excitation and sensing devices through an umbilical connector similar to that discussed above with reference to FIGS. 1 and 2.

Numerous variations and combinations of the features discussed above may be utilized without departing from the present invention as defined by the claims. For example, the supports for the devices discussed above may be formed as flexible circuits such as flexible polyimide circuits with flexible copper traces thereon. Also, the devices may be provided with visible markings other than the suture eyes depicted in FIGS. 1 and 2. Multiple devices may be used in a single procedure. These may be placed edge-to-edge to cover a large lesion, or else may be placed at spaced apart locations to treat widely separated lesions. The array of selectively actuable light emitting diodes discussed above can be replaced by an array of selectively actuable light blocking elements and a continuous light-emitting layer. For example, individual electrically operated liquid crystal light blocking elements may overlie a continous light emitting layer such as a phosphor layer or a fluorescent illumination source. Also, the light emitted at the surface of the device may be provided by a light source disposed outside of the device itself. The light is supplied to the device by a fiber optic arrangement disposed in the umbilical connector. As these and other variations and other combinations of the features discussed above can be utilized, the foregoing description of the preferred embodiment should be taken by way of illustration rather than by limitation of the invention set forth in the claims.

We claim:

1. A method of administering photodynamic therapy to a mammalian subject having a lesion comprising the steps of:

(a) positioning a light-applying device capable of applying light throughout an application area over the lesion so that the application area of the device covers the lesion and also covers some normal tissue of the subject;

(b) detecting the extent of the lesion using sensors disposed on said light-applying device; and (c) actuating the device and controlling actuating the device responsive to the detected extent to apply treating light at a treatment wavelength selectively in areas of the application area aligned with the lesion and to not apply light in areas of the application area aligned with normal tissue.

2. A method as claimed in claim 1 wherein said detecting step includes the step of detecting luminescence from tissues of the subject.

3. A method as claimed in claim 2 further comprising the steps of administering a luminescent agent having an affinity for the lesion and an affinity for normal tissue different from said affinity for the lesion and the step of exciting luminescence of said agent and said detecting step including detecting the luminescence of said agent.

4. A method as claimed in claim 3 wherein said luminescent agent is a photosensitizing agent.

5. A method as claimed in claim 3 further comprising the step of exciting luminescence of said luminescent agent by applying light at an excitation wavelength different from said treatment wavelength.

6. A method as claimed in claim 5 wherein said step of applying light at said excitation wavelength includes the step of providing a source of light at said excitation wavelength on said light applying device.

7. A method as claimed in claim 1 further comprising the step of administering a photosensitizing agent to the subject before applying said treating light.

* * * * *